United States Patent
Majeed et al.

(10) Patent No.: US 11,957,728 B2
(45) Date of Patent: *Apr. 16, 2024

(54) COMPOSITIONS FOR TARGETING RECEPTOR FOR ADVANCED GLYCATION END-PRODUCTS (RAGE) IN A CHRONIC INFLAMMATORY CONDITION

(71) Applicants: Muhammed Majeed, Bangalore (IN); Kalyanam Nagabhushanam, East Windsor, NJ (US); Lakshmi Mundkur, Bangalore (IN)

(72) Inventors: Muhammed Majeed, Bangalore (IN); Kalyanam Nagabhushanam, East Windsor, NJ (US); Lakshmi Mundkur, Bangalore (IN)

(73) Assignee: Sami-Sabinsa Group Limited, Bangalore (IN)

(*) Notice: Subject to any disclaimer, the term of this patent is extended or adjusted under 35 U.S.C. 154(b) by 0 days.

This patent is subject to a terminal disclaimer.

(21) Appl. No.: 17/552,491

(22) Filed: Dec. 16, 2021

(65) Prior Publication Data

US 2022/0193005 A1 Jun. 23, 2022

Related U.S. Application Data

(60) Provisional application No. 63/126,920, filed on Dec. 17, 2020.

(51) Int. Cl.
*A61K 36/9066* (2006.01)
*A23L 33/105* (2016.01)
(Continued)

(52) U.S. Cl.
CPC ........ *A61K 36/9066* (2013.01); *A23L 33/105* (2016.08); *A61K 9/0053* (2013.01);
(Continued)

(58) Field of Classification Search
CPC ....... A23L 33/105; A61K 31/12; A61K 31/23; A61K 36/9066; A61K 47/12; A61K 47/26;
(Continued)

(56) References Cited

U.S. PATENT DOCUMENTS

| | | |
|---|---|---|
| 9,782,364 B1 | 10/2017 | Cavaleri |
| 2016/0166516 A1* | 6/2016 | Gannon ............... A61K 9/4858 514/679 |
| 2019/0183892 A1* | 6/2019 | Meixueiro-Montes-de-Oca ......... A61K 31/352 |

OTHER PUBLICATIONS

Chhipa et al., Targeting receptors of advanced glycation end products (RAGE): Preventing diabetes induced cancer and diabetic complications, Pathology—Research and Practice, vol. 215, 1-14, 2019 (Year: 2019).*

(Continued)

*Primary Examiner* — Kortney L. Klinkel
*Assistant Examiner* — Padmaja S Rao

(57) ABSTRACT

The invention discloses compositions and methods comprising enriched Bisdemethoxycurcumin (BDMC) present not less than 20% w/w for use in inhibiting Receptor for Advanced Glycation End-Products (RAGE) expression in a subject with chronic-inflammatory condition. The composition further comprises β-amyrin palmitate (BAP). The invention also includes disclose the use of the above composition in the management of chronic inflammatory condition in a subject.

22 Claims, 1 Drawing Sheet
Specification includes a Sequence Listing.

(51) Int. Cl.
- *A61K 9/00* (2006.01)
- *A61K 9/20* (2006.01)
- *A61K 9/48* (2006.01)
- *A61K 31/12* (2006.01)
- *A61K 31/19* (2006.01)
- *A61K 31/23* (2006.01)
- *A61K 36/324* (2006.01)
- *A61K 47/12* (2006.01)
- *A61K 47/26* (2006.01)
- *A61K 47/42* (2017.01)
- *A61P 3/06* (2006.01)
- *A61P 19/02* (2006.01)
- *A61P 39/06* (2006.01)

(52) U.S. Cl.
CPC .......... *A61K 9/0056* (2013.01); *A61K 9/2009* (2013.01); *A61K 9/2013* (2013.01); *A61K 9/2054* (2013.01); *A61K 9/2059* (2013.01); *A61K 9/4866* (2013.01); *A61K 31/12* (2013.01); *A61K 31/19* (2013.01); *A61K 31/23* (2013.01); *A61K 36/324* (2013.01); *A61K 47/12* (2013.01); *A61K 47/26* (2013.01); *A61K 47/42* (2013.01); *A61P 3/06* (2018.01); *A61P 19/02* (2018.01); *A61P 39/06* (2018.01)

(58) Field of Classification Search
CPC .... A61K 47/42; A61K 9/0056; A61K 9/2009; A61K 9/2013; A61K 9/2054; A61K 9/2059; A61K 9/4866; A61K 36/71; A61K 2300/00; A61P 19/02; A61P 39/06
See application file for complete search history.

(56) References Cited

OTHER PUBLICATIONS

Nair et al., Promising anti-diabetes mellitus activity in rats of B-amyrin palmitate isolated from Hemidesmus indicus roots, European Journal of Pharmacology, vol. 734, 77-82, Apr. 12, 2014 (Year: 2014).*

Mohammadi et al., The Effect of Curcumin on TNF-α, IL-6 and CRP Expression in a Model of Polycystic Ovary Syndrome as an Inflammation State, Journal of Reproduction and Infertility, vol. 18, No. 4, 352-360, 2017 (Year: 2017).*

Tang et al., Curcumin ameliorates chronic obstructive pulmonary disease by modulating autophagy and endoplasmic reticulum stress through regulation of SIRT1 in a rat model, Journal of International Medical Research, vol. 47, No. 10, 4764-4774, 2019 (Year: 2019).*

Yodkeeree et al., Curcumin, demethoxycurcumin and bisdemethoxycurcumin differentially inhibit cancer cell invasion through the down-regulation of MMPs and uPA, Journal of Nutritional Biochemistry 20 (2009) 87-95.

Gordon et al., Oxidative Transformation of Demethoxy- and Bisdemethoxycurcumin: Products, Mechanism of Formation, and Poisoning of Human Topoisomerase IIα, Chem Res Toxicol. May 18, 2015; 28(5): 989-996.

Jayaprakasha et al. Antioxidant activities of curcumin, demethoxycurcumin and bisdemethoxycurcumin, Food Chemistry 98 (2006) 720-724.

Sandur et al. Curcumin, demethoxycurcumin, bisdemethoxycurcumin, tetrahydrocurcumin and turmerones differentially regulate anti-inflammatory and anti-proliferative responses through a ROS-independent mechanism, Carcinogenesis vol. 28 No. 8 pp. 1765-1773, 2007.

* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: ARTIFICIAL SEQUENCE
<220> FEATURE:
<223> OTHER INFORMATION: FORWARD PRIMER FOR RAGE

<400> SEQUENCE: 1
acagaaaccg gtgatgaagg                                           20

<210> SEQ ID NO 2
<211> LENGTH: 20
<212> TYPE: DNA
<213> ORGANISM: ARTIFICIAL SEQUENCE
<220> FEATURE:
<223> OTHER INFORMATION: REVERSE PRIMER FOR RAGE

<400> SEQUENCE: 2
ctctcctcga gtctgggttg                                           20

<210> SEQ ID NO 3
<211> LENGTH: 19
<212> TYPE: DNA
<213> ORGANISM: ARTIFICIAL SEQUENCE
<220> FEATURE:
<223> OTHER INFORMATION: FORWARD PRIMER FOR BETA ACTIN

<400> SEQUENCE: 3
cccgcgagta caaccttct                                            19

<210> SEQ ID NO 4
<211> LENGTH: 18
<212> TYPE: DNA
<213> ORGANISM: ARTIFICIAL SEQUENCE
<220> FEATURE:
<223> OTHER INFORMATION: REVERSE PRIMER FOR BETA ACTIN

<400> SEQUENCE: 4
cgtcatccat ggcgaact                                             18

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: FORWARD PRIMER FOR TNF ALPHA

<400> SEQUENCE: 5
actgaacttc ggggtgattg                                           20

<210> SEQ ID NO 6
<211> LENGTH: 20
<212> TYPE: DNA
<213> ORGANISM: ARTIFICIAL SEQUENCE

```
<220> FEATURE:
<223> OTHER INFORMATION: REVERSE PRIMER FOR TNF ALPHA

<400> SEQUENCE: 6
gcttggtggt ttgctacgac                                            20

<210> SEQ ID NO 7
<211> LENGTH: 21
<212> TYPE: DNA
<213> ORGANISM: ARTIFICIAL SEQUENCE
<220> FEATURE:
<223> OTHER INFORMATION: FORWARD PRIMER FOR IL6

<400> SEQUENCE: 7
ctctccgcaa gagacttcca g                                          21

<210> SEQ ID NO 8
<211> LENGTH: 21
<212> TYPE: DNA
<213> ORGANISM: ARTIFICIAL SEQUENCE
<220> FEATURE:
<223> OTHER INFORMATION: REVERSE PRIMER FOR IL6

<400> SEQUENCE: 8
ttctgacagt gcatcatcgc t                                          21

<210> SEQ ID NO 9
<211> LENGTH: 23
<212> TYPE: DNA
<213> ORGANISM: ARTIFICIAL SEQUENCE
<220> FEATURE:
<223> OTHER INFORMATION: FORWARD PRIMER FOR IL1 BETA

<400> SEQUENCE: 9
caccttcttt tccttcatct ttg                                        23

<210> SEQ ID NO 10
<211> LENGTH: 23
<212> TYPE: DNA
<213> ORGANISM: ARTIFICIAL SEQUENCE
<220> FEATURE:
<223> OTHER INFORMATION: REVERSE PRIMER FOR IL1 BETA

<400> SEQUENCE: 10
gtcgttgctt gtctctcctt gta                                        23
```

COMPOSITIONS FOR TARGETING RECEPTOR FOR ADVANCED GLYCATION END-PRODUCTS (RAGE) IN A CHRONIC INFLAMMATORY CONDITION

CROSS REFERENCE TO RELATED APPLICATIONS

This is a non-provisional application claiming priority from U.S. provisional application No. 63/126,920 filed on 17 Dec. 2020, the contents of which are incorporated herein by reference.

FIELD OF INVENTION

The invention in general relates to compositions for use and method for inhibiting Receptor for Advanced Glycation End-Products (RAGE) expression in a subject with chronic-inflammatory condition using a composition comprising enriched Bisdemethoxycurcumin (BDMC) present not less than 20% w/w. The composition further comprises β-amyrin palmitate (BAP). The invention also includes therapeutically managing chronic inflammatory condition in a subject using the above composition.

BACKGROUND OF INVENTION

The nonenzymatic oxidation of proteins and the glycation reactions leads to the formation of a advanced glycation end products (AGEs). Advanced renal failure, atherosclerosis, diabetes, and aging are some conditions where AGEs are formed. They are increased in inflammatory conditions such as systemic lupus erythematosus, rheumatoid arthritis, osteoarthritis, and dialysis-related complications suggesting their inherent association with chronic inflammatory diseases. These chronic inflammatory conditions can increase the risk of accelerated atherosclerosis and its complications. Conversely, hypoxia and ischemia-reperfusion injuries are rapid generators of AGEs and can further increase the complications of inflammatory diseases. Hyperglycemia or diabetes results in elevated blood glucose level in the blood stream, is a condition which facilitates the formation of advanced glycation end products (AGEs). The excessive exposure of cells to glucose results in glucose induced inflammation and other associated pathological disorders, whose mechanism is yet to be established. And the existing hypothesis alludes to deposits of AGEs in tissues leading to organ failures (Lin et al. *Curcumin inhibits gene expression of receptor for advanced glycation end-products (RAGE) in hepatic stellate cells in vitro by elevating PPARγ activity and attenuating oxidative stress, British Journal of Pharmacology* 2212-2227 (2012)). AGEs are diverse macromolecules, among them are carboxymethyl lysine (CML), carboxyethyl lysine (CEL), pentosidine, glucosepane, glyoxal lysine dimer, and glycolic acid lysine amide, and formed by the non-enzymatic process of glycation of proteins and lipids. AGES induce their cellular effects by interacting with their receptors. The Receptor for Advanced Glycation End products (RAGE) is an ubiquitous, transmembrane, receptor which binds to a range of endogenous ligands. The interaction between AGE and RAGE initiates a complex intracellular signaling cascade resulting in the production of reactive oxygen species (ROS), immunoinflammatory effects, cellular proliferation or apoptosis with concomitant upregulation of RAGE itself. Several studies have discovered a correlation between RAGE activity and pathological conditions, such as cancer, diabetes, cardiovascular diseases and neurodegeneration. While AGE may be benign and nonreactive, several studies have discovered a correlation between RAGE activity and pathological conditions, such as cancer, diabetes, cardiovascular diseases and neurodegeneration it may be the cause of complications in chronic diseases such as, type II diabetes mellitus, cardiovascular diseases Alzheimer's disease, cancer, peripheral neuropathy, sensory losses and blindness (Rehman et al. Effect of non-enzymatic glycosylation in the epigenetics of cancer, Semin Cancer Biol. Dec 2:S 1044-579X(20) 30257 (2020); (Laura et al. *The AGE-RAGE Axis: Implications for Age-Associated Arterial Diseases. Frontiers in Genetics,* 8, 1-10 (2017)). The mechanism of action resulting from binding of AGE-RAGE leads to stimulation of NADPH oxidase, increasing the production of reactive oxygen species (ROS), and thereby regulating the expression of tumor necrosis factor (TNF-α), transcription factor nuclear factor-κB (NF-κB), release of cytokines, inflammatory expression, and activation of cellular signal transduction. The ROS generated during RAGE activation is a source for the protein oxidation forming protein carbonyl species. Direct oxidation of side chains of lysine, arginine, proline, and threonine residues, among other amino acids, in the "primary protein carbonylation" reaction produces DNPH detectable protein products termed as reactive carbonyl species (RCS) (Suzuki et al. Protein carbonylation. *Antioxid Redox Signal.* 2001; 12(3).323-325.). On the contrary, the reactive carbonyls of sugars combine with amino groups of a protein, lipid or nucleic acid generating Schiff bases, which rearrange to Amadori products. In a series of slow reactions, the Amadori reactions, Schiff base and Maillard reactions, ultimately form AGE. Amadori compound can further degrade to different advanced glycation end products including reactive α-dicarbonyls with a release of ROS such as superoxide anion and hydrogen peroxide. The α-dicarbonyls formed via oxidative degradation of Schiff base and Amadori adducts as well as during glucose autoxidation can result in oxidative deamination of Lys via Strecker-type reaction, leading to the formation of 3-Deoxyglucosone (3DG) and methylglyoxal (MG) (Ros et al. *Protein Carbonylation (Principles, Analysis, and Biological Implications) Diversity of Protein Carbonylation Pathways,* 48-8 (2017)). The α-Dicarbonyls compounds are also generated in vivo during lipid peroxidation, autoxidation of glucose or the glucose metabolism. Reaction of glyoxal GO) and methylglyoxal (MGO) with lysine and arginine residues in proteins give rise to the formation of AGES such as carboxymethyllysine (CML), carboxyethyllysine (CEL) and argpyrimidine (ArgP). Thus the formation of AGE, protein carbonyls and their interaction with RAGE and downstream oxidative stress and inflammation are closely linked. Increase in the steady-state levels of RCS and AGES results in carbonyl stress disturbing normal metabolism. RCS are ubiquitous compounds with relatively high half-life time and stability, especially if compared with reactive oxygen species (ROS). Low molecular mass, noncharged structure, and relatively high stability of RCS allow them to cross biological membranes, diffuse through the peripheral circulation and even cross blood brain barrier. The glycation-derivative RCS as methylglyoxal, glyoxal, 3-deoxyfructose, glucosone, and 3-deoxyglucosone are about 20,000-fold more reactive than reducing carbohydrates. Alzheimer's disease (AD), rheumatoid arthritis, diabetes, sepsis, chronic renal failure, and respiratory distress syndrome are some of the conditions where protein carbonylation is increased (Isabella et al Protein carbonyl groups as biomarkers of oxidative stress, 329(1), 23-38 (2003)). The formation of AGE is accelerated under hyperglycemia, oxidative stress, aging and inflammation (Laura et al. *The AGE-RAGE Axis: Implications for Age Associated Arterial Diseases, Frontiers in Genetics,* 8, 1-10 (2017)). While AGE may be benign and nonreactive, it may be the cause of complications in chronic diseases such as, type II diabetes mellitus, cardiovascular diseases Alzheimer's disease, cancer, peripheral neuropathy, sensory losses and blindness (Rehman et al. Effect of non-enzymatic glycosylation in the epigenetics of cancer, Semin Cancer Biol. Dec 2:S1044-579X(20) 30257 (2020)). Reducing glycation, RAGE expression and protein carbonylation can ultimately reduce the oxidative and carbonyl stress which may be beneficial in chronic inflammatory conditions. RAGE is an attractive target for the development of inhibitors for the management of these conditions, as a potential biomarker for several diseases. Altered circulating levels of RAGE has been identified in patients with diabetic complications, cardiovascular diseases and Alzheimer's disease. RAGE has been investigated a s a potential target for therapy in cancer, cardiovascular diseases and neurodegeneration. (Salvatore et al. Targeting the Receptor for Advanced Glycation End products (RAGE): A Medicinal Chemistry Perspective, 60(17), 7213-7232 (2017))

There are numerous studies suggesting diabetes mediated atherosclerosis by implicating the role of RAGE in atherosclerosis lesion formation and promoting proinflammatory pathways. In a study, diabetes linked increase in AGE was significantly reduced in diabetic RAGE$^{-/-}$apoE$^{-/-}$ mice along with inflammatory responses with decreased macrophages accumulation, expression of cytokines and chemokines (Paavonen et al. *Receptor for Advanced Glycation End Products (RAGE) Deficiency Attenuates the Development of Atherosclerosis in Diabetes, Diabetes,* 57, 2461-2469 (2008)). This was also supported by numerous studies showing that the inhibition of RAGE activation using neutralizing antibodies or soluble RAGE (Park et al. *Suppression of accelerated diabetic atherosclerosis by the soluble receptor for advanced glycation end products. Nat Med* 4, 1025-1031 (1998); Bucciarelli et al. *RAGE blockade stabilizes established atherosclerosis in diabetic apolipoprotein E-null mice. Circulation* 106, 2827-2835 (2002); Sakaguchi et al. *Central role of RAGE-dependent neointimal expansion in arterial restenosis. J Clin Invest* 111, 959-972 (2003)).

Role of curcumin in attenuating effects in RAGE signalling, inhibition of AGEs accumulation and expression of RAGE in experimental diabetic rats has been reported (Lin et al. Curcumin inhibits gene expression of receptor for advanced glycation end products (RAGE) in hepatic stellate cells in vitro by elevating PPARγ activity and attenuating oxidative stress, British Journal of Pharmacology 166, 2212-2227 (2012); Yu et al. Curcumin Alleviates Diabetic Cardiomyopathy in Experimental Diabetic Rats. PLOS One 7(12) 1-11)). But curcumin that is commercially available includes three curcuminoids, 72 to 77% curcumin, 14 to 18% dimethoxy curcumin, and 3 to 5% bisdemethoxycurcumin. And larger fraction of curcumin makes it hydrophobic and thereby affecting bioavailability and absorption (Pushpakumari et al. Enhancing the Absorption of Curcuminoids from Formulated Turmeric Extracts, 6(6) 2468-2476 (2015)). The biological properties of curcumin, bisdemethoxycurcumin and demethoxycurcumin vary in different diseases conditions and recently bisdemethoxycurcumin and demethoxycurcumin are garnering the much attention owing to their similar and superior efficacy over curcumin in managing certain disease conditions. (Majeed et al., Reductive Metabolites of Curcuminoids, Nutriscience Publishers LLC, 2019). The pharmacological challenge associated with targeting RAGE involves not only controlling the gene expression of inflammatory gene, but also controlling NF-κB activation, which induces expression of RAGE in a feed forward loop (Armando et al. *Inhibition of RAGE Axis Signalling: A Pharmacological Challenge, Current Drug Targets,* 20, 340-346. (2019)). There have been promising results with blocking peptides and antibodies raised against RAGE, but facing limited use due its limitations as a therapeutic compound (Arumugam T et al. S100P-derived RAGE antagonistic peptide reduces tumor growth and metastasis. Clin Cancer Res. 18(16): 4356-64 (2012); Kokkola et al. Successful treatment of collagen-induced arthritis in mice and rats by targeting extracellular high mobility group box chromosomal protein 1 activity. Arthritis Rheum 48(7): 2052-8 (2003)). Also, several small molecules such as TTP488, Azeliragon, Pioglitazone, a PPARγ agonist also blocks RAGE signaling (Salvatore et al. *Targeting the Receptor for Advanced Glycation End products (RAGE): A Medicinal Chemistry Perspective.* 60(17), 7213-7232 (2017): Burstein et al. *Effect of TTP488 inpatients with mild to moderate Alzheimer's disease. BMC Neurol.* 14, 12 (2014); Burstein et al. *Development of azeliragon, an oral small molecule antagonist of the receptor for advanced glycation end products, for the potential slowing of loss of cognition in mild Alzheimer's disease, J Prev Alzheimers Dis* 5(2): 149-54 (2018)). Considering the complexity associated with targeting RAGE and with a very limited list of compounds in the clinical trials, there is a need for novel ways to targeting RAGE especially those that are safe, less toxic.

OBJECTIVES OF THE INVENTION

It is the main objective of the invention to disclose a composition for use and method of inhibiting RAGE expression in a subject with chronic inflammatory condition, using a composition comprising enriched Bisdemethoxycurcumin (BDMC) present not less than 20% w/w. The composition further comprises β-amyrin palmitate (BAP).

In yet another main objective of the invention to disclose a composition for use and method of therapeutically managing RAGE in a subject with chronic inflammatory condition with a composition comprising enriched Bisdemethoxycurcumin (BDMC) present not less than 20% w/w. The composition further comprises β-amyrin palmitate (BAP).

SUMMARY

The invention broadly solves the aforementioned problems mentioned in the background by covering a method and composition for use in inhibiting RAGE expression in a subject with chronic inflammatory condition using a composition comprising enriched Bisdemethoxycurcumin (BDMC) present not less than 20% w/w. The composition further comprises β-amyrin palmitate (BAP).

The first aspect of the invention relates to a composition for use in inhibiting RAGE expression in a subject with chronic inflammatory condition with a composition comprising enriched Bisdemethoxycurcumin (BDMC) present not less than 20% w/w. The composition further comprises β-amyrin palmitate (BAP).

In yet another aspect of the invention covers a composition for use in therapeutically managing chronic inflammatory condition in a subject, with a composition comprising enriched Bisdemethoxycurcumin (BDMC) present not less than 20% w/w. The composition further comprises β-amyrin palmitate (BAP).

In another aspect of the invention covers a method for inhibiting RAGE expression in a subject with chronic inflammatory condition, with a composition comprising enriched Bisdemethoxycurcumin (BDMC) present not less than 20% w/w. The composition further comprises β-amyrin palmitate (BAP).

In another aspect of the invention covers a method for treating chronic inflammatory condition in a subject, administering said subject with a composition comprising enriched Bisdemethoxycurcumin (BDMC) present not less than 20% w/w. The composition further comprises β-amyrin palmitate (BAP).

The broader scope of applicability of the present invention will be apparent from the detailed description below. However, it should be understood that the detailed description and specific examples below, while indicating preferred embodiments of the invention should not be construed as the limitations to the invention, and it is within the scope of those skilled in the art to make various changes and modifications, such as changing the concentration range of samples used, derivatives/analogs of curcuminoids, BAP, experimental conditions, choice of mammals, are well within the spirit and scope of the invention from this detailed description.

DESCRIPTION OF PREFERRED EMBODIMENTS

Selected Definitions

Figure 1:
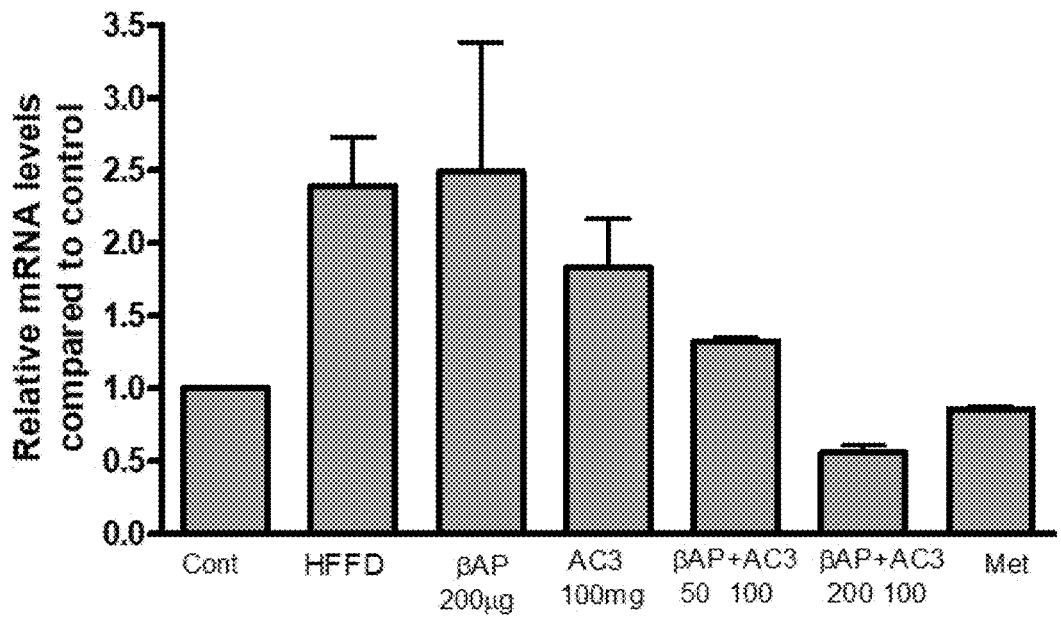
FIG. 1 shows effect of AC3, BAP, and their combinations on the expression of RAGE in pancreas. *P<0.05.

All the terms used in this application carry ordinary meaning as known in the prior art unless otherwise specified. Few other specific definitions used in this invention are explained below, which applies throughout this specification. Claims provide broader definition unless and otherwise specified.

In this application, any reference to sample refers to either one or combination of the following agents, which brings about the disclosed therapeutic effect. The agents include, enriched BDMC composition refers to curcuminoids composition comprising at least 20% w/w of BDMC. More specifically, AC3 is the preferred curcuminoids used in the invention and any reference to curcuminoids is AC3, which is 20-50% w/w bisdemethoxycurcumin, 10-25% w/w demethoxycurcumin and 30-50% w/w curcumin, and BAP refers to β-amyrin palmitate. Any reference to C3 complex, which is 75-81% curcumin, 15-19% demethoxycurcumin, and 2.2-6.5% bisdemethoxycurcumin. Also, curcuminoids refer to either BDMC, DMC, or AC3 depending on the example disclosed.

Therapeutically managing or management refers to a condition of effectively ameliorating conditions disclosed in the invention. Any reference to control in this specification refers to diabetic control, untreated control, Metformin control on the experiment and examples covered.

The invention in general covers a method and composition for use in inhibiting RAGE expression in a subject with a chronic inflammatory condition, with a composition comprising enriched Bisdemethoxycurcumin (BDMC) present not less than 20% w/w. The invention also covers a composition for use in therapeutically managing chronic inflammatory condition in a subject, with a composition comprising enriched Bisdemethoxycurcumin (BDMC) present not less than 20% w/w. Further, it also covers a method for treating chronic inflammatory condition in a subject, administering said subject with a composition comprising enriched Bisdemethoxycurcumin (BDMC) present not less than 20% w/w. Wherein the composition comprises of 20-50% w/w BDMC, 10-25% w/w demethoxycurcumin (DMC) and 30-50% w/w curcumin, with the total curcuminoids in the composition are in the range of 20-95% w/w The composition further comprises β-amyrin palmitate (BAP). In a related aspect, the subject is a mammal.

In the most preferred embodiment, the invention discloses a composition for use in inhibiting RAGE expression in a subject with chronic inflammatory condition, wherein the composition comprises enriched Bisdemethoxycurcumin (BDMC) present not less than 20% w/w. In another aspect of this embodiment, the composition comprises of 20-50% w/w BDMC, 10-25% w/w demethoxycurcumin (DMC) and 30-50% w/w curcumin, with the total curcuminoids in the composition are in the range of 20-95% w/w. In a related aspect of this embodiment, the composition further comprises β-amyrin palmitate (BAP). In a related aspect, the subject is a mammal.

In another most preferred embodiment of the invention, the invention discloses a composition for use in therapeutically managing chronic inflammatory condition in a subject, wherein the composition comprises enriched Bisdemethoxycurcumin (BDMC) present not less than 20% w/w. In another aspect of this embodiment, the composition comprises of 20-50% w/w BDMC, 10-25% w/w demethoxycurcumin (DMC) and 30-50% w/w curcumin, with the total curcuminoids in the composition are in the range of 20-95% w/w. In a related aspect of this embodiment, the composition further comprises β-amyrin palmitate (BAP). In a related aspect, the subject is a mammal.

In another most preferred embodiment of the invention, the invention discloses a method for inhibiting RAGE expression in a subject with chronic inflammatory condition, comprising (a) identifying said subject with chronic inflammatory condition; b) administering said subject with a composition comprising enriched Bisdemethoxycurcumin (BDMC) present not less than 20% w/w. In another aspect of this embodiment, the composition comprises of 20-50% w/w BDMC, 10-25% w/w demethoxycurcumin (DMC) and 30-50% w/w curcumin, with the total curcuminoids in the composition are in the range of 20-95% w/w. In a related aspect of this embodiment, the composition further comprises β-amyrin palmitate (BAP). In a related aspect, the subject is a mammal.

In yet another most preferred embodiment of the invention, the invention discloses a method treating chronic inflammatory condition in a subject, comprising (a) identifying said subject with chronic inflammatory condition; b) administering said subject with a composition comprising enriched Bisdemethoxycurcumin (BDMC) present not less than 20% w/w. In another aspect of this embodiment, the composition comprises of 20-50% w/w BDMC, 10-25% w/w demethoxycurcumin (DMC) and 30-50% w/w curcumin, with the total curcuminoids in the composition are in the range of 20-95% w/w. In a related aspect of this embodiment, the composition further comprises β-amyrin palmitate (BAP). In a related aspect, the subject is a mammal.

Figure 2:
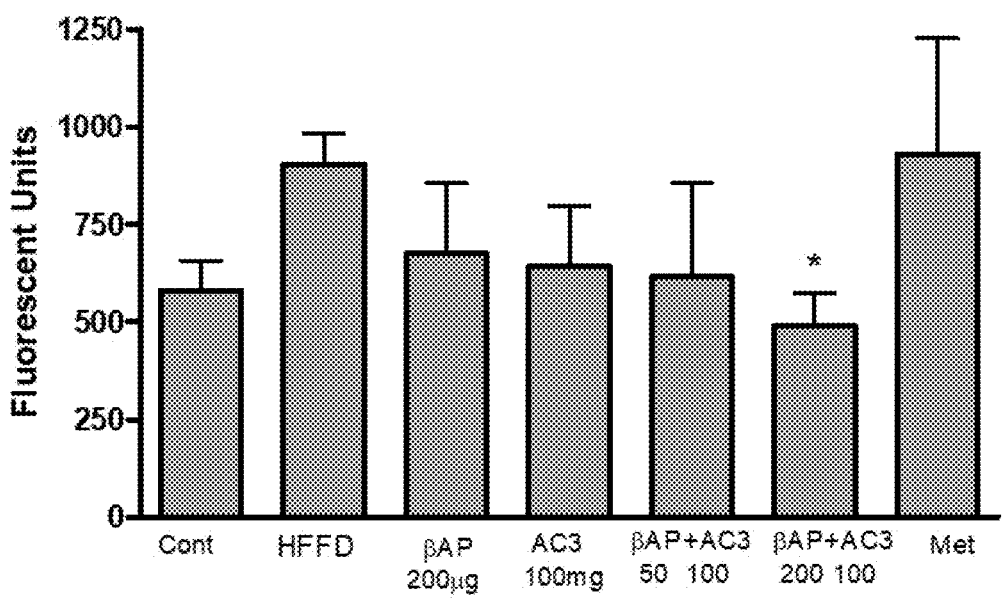
FIG. 2 shows effect of AC3, BAP, and their combinations on the effect of anti-glycation in pancreas. *P<0.05.

In related embodiments of the invention, inhibiting RAGE expression in a subject with chronic inflammatory condition is brought about by decreasing expression of inflammatory markers, decreasing oxidative stress, and moderating glycation levels. Further aspect of this embodiment, the inhibition of RAGE is brought about by curcuminoids, BAP, or their combination selected from the range of 1-10 μg/mL or preferably from 2-8 μg/mL, or preferably 4-6 μg/mL (Example 1, Tables 1-3). In another related aspect of this embodiment, wherein moderation of RAGE expression is brought about by curcuminoids. BAP, or their combination resulting in decrease of RAGE expression. RAGE expression was increased in diabetic rats. BAP had no effect on pancreatic RAGE expression AC3 reduced the expression by 30.3%. The combination reduced expression by 44.6 and 76.7% respectively While metformin was effective in reducing by 6.9 (FIG. 1, Example 3). In related aspect of this embodiment of the invention, decrease of the inflammatory marker (TNF-α, IL6, IL-1β) expression is brought about by treating with curcuminoids, BAP, or combination. The combinations showed 20-50-fold decrease compared to diabetic control, and the effect was more pronounced when 100 mg/kg of curcuminoids and 200 μg/kg of BAP was used compared to the individual treatment (Table 6, Example 3). In another aspect of this embodiment of the invention, oxidative stress is decreased in the subject, and brought about by curcuminoids, BAP, or their combination. The combinations had a better effect with 3-4 fold decrease compared to the BAP with 2 fold decrease from the diabetic control (Table 7, Example 4). In another aspect of this embodiment of the invention, moderation of glycan levels is brought about by treating with curcuminoids, BAP, or combination. The effect of Protein carbonylation was inhibited between 6 to 10-fold when either curcuminoids or BAP are used individually, and the combination provided 20 fold change from the hyperglycemic control (FIG. 2, Example 5). In a related aspect, the subject is a mammal.

In related embodiments of the invention therapeutic effects in a subject are brought about by treating with curcuminoids, BAP from the range of 50 μg/kg to 100 mg/kg. More preferably curcuminoids between 1-100 mg/kg, or more preferably between 50-100 mg/kg or most preferably 100 mg/kg. BAP is selected from the range of 50-200 μg/kg, or more preferably 50 μg/kg or most preferably at either 50 μg/kg or 200 μg/kg. The combination of curcuminoids and BAP are selected from the range of 50 μg/kg to 100 mg/kg, or more preferably BAP either at 50 μg/kg or 200 μg/kg and curcuminoids at 100 mg/kg. In related embodiments of the invention chronic inflammatory condition is selected from the group consisting of type II diabetes mellitus, cardiovascular diseases Alzheimer's disease, cancer, peripheral neuropathy, sensory losses and blindness. In a related aspect, the subject is a mammal.

In another related embodiment of the invention, wherein the composition further comprises of stabilizing agents, bioavailability enhancers and antioxidants, pharmaceutically or nutraceutically or cosmeceutically accepted excipients and enhancers and suitably formulated to be administered orally in the form of tablets, capsules, syrups, gummies, powders, suspensions, emulsions, chewables, candies or eatables (Example 7). It is well within the scope of a person skilled in the art to come up with a suitable formulation for administration In another embodiment of the invention discloses inhibition of DPP4 (Dipeptidyl-peptidase 4), α-glucosidase, and anti-glcyation using AC3, C3, or individual curcuminoids composition (Tables 8-11).

Other modifications and variations of the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

EXAMPLES

Example 1: Antiglycation—A Measure of Preventing Advanced Glycation End Products In Vitro Glycation is the non-enzymatic glycosylation reaction involving amino groups of proteins, lipids, or nucleic acids with sugar aldehyde or keto groups resulting in the formation of advanced glycosylation end-products (AGE) (Yamagishi et al. Pathologic role of dietary advanced glycation end products in cardiometabolic disorders, and therapeutic intervention, Nutrition, 32(2), 157-65 (2016)). The reactive carbonyls of sugars combine with amino groups of a protein, lipid or nucleic acid generating Schiff bases, which rearrange to Amadori products. In a series of slow reactions, the Amadori reactions, Schiff base and Maillard reactions, ultimately form AGE. Although glycation is slow in vivo, the glycation products have long-lasting effects. The effect of test substances on preventing the formation of AGE was evaluated in vitro Anti-glycation activity was evaluated as described earlier (Sero et al. Tuning a 96-Well Microtiter Plate Fluorescence-Based Assay to Identify AGE Inhibitors in Crude Plant Extracts) Briefly, 10 μl of various sample concentrations were added to 40 μl of 25 mg/ml bovine serum albumin and 50 μl of 150 mg/ml D-Ribose in a 96 well black microplate. D-Ribose with buffer served as control. The plate containing the mixture was incubated for 24 h at 37° C. The advanced glycation product was detected by measuring the fluorescence intensity at Ex/Em of 390/460 nm by using BMG FLUOstar Optima Microplate reader. The formation of AGE (non enzymatic reaction between protein (BSA) and sugar (ribose)) was inhibited by AC3 in a concentration dependent manner (Table 2). BAP was a poor inhibitor of AGE formation (Table 1). Combination of AC3 and BAP could synergistically increase the inhibition of glycation in vitro (Table 3).

Tables 1 & 2: Concentration dependent inhibition of BAP and AC3

| Conc. BAP (μg/mL) | Percentage Inhibition |
|---|---|
| 1 | 0 |
| 2 | 11.92 |
| 4 | 9.67 |

| Conc. AC3 (μg/mL) | Percentage Inhibition |
|---|---|
| 4 | 11.10 |
| 6 | 17.91 |
| 8 | 16.48 |

TABLE 3

Concentration dependent inhibition of AC3 BAP combination

| Conc. AC3:BAP(µg/mL) | Percentage Inhibition |
|---|---|
| 4:1 | 21.04 |
| 4:2 | 16.71 |
| 4:4 | 22.37 |

Example 2: Inhibition of Age and RAGE in Physiological Conditions Taking the Example of Diabetes To study the effect of AGE and RAGE interaction and their pathological consequences, diet induced diabetes was used as a model.

Wistar Rats (150 g) were given High fat and fructose diet (HFFD) to induced type 2 diabetes (T2D). HFFD induces the development of diabetes associated with long term metabolic disorders including Fasting hyperglycemia, pre- and post-prandial hyperinsulinemia, Insulin resistance, Glucose intolerance and Dyslipidemia. Animals in HFFD show complications associated with T2D such as hepatic steatosis complicated by fibrosis, inflammation, hyperleptinemia and endothelial dysfunction.

Rats were co administered with AC3 (100 mg/kg), BAP (200 µg/kg) BAP+AC3 (200 µg+100 mg/kg) BAP+AC3 (50 µg+100 mg/kg) and Metformin as positive control at 100 mg/kg along with HFFD for 90 days (Table 4). The organs were collected at the end of the experiment to evaluate the effect of the supplements on RAGE expression, oxidative stress and inflammation.

TABLE 4

Study Group Animals (Rats)

| Group No | Treatment group | Dose | No. of animals |
|---|---|---|---|
| 1 | Control | — | 6 |
| 2 | HFFD control | High fat and fructose induced hyperglycaemia | 6 |
| 3 | BAP | 200 µg/kg | 6 |
| 4 | AC3 | 100 mg/kg | 6 |
| 5 | AC3 + BAP | 100 mg/kg + 50 µg/kg | 6 |
| 6 | AC3 + BAP | 100 mg/kg + 200 µg/kg | 6 |
| 7 | Metformin Positive control | 100 mg/kg | 6 |

Example 3: RAGE Expression in Pancreas

DNA was extracted from pancreas sample using the trizol method. The pancreas tissues were homogenized in liquid nitrogen followed by trizol extraction and DNAse to remove any traces of DNA. First-strand cDNA was prepared from RNA samples using oligo dT primers and Superscript III reverse transcriptase (cDNA synthesis kit, Invitrogen™) Quantitative real-time PCR (qRT-PCR) was performed with SYBR Green I fluorescent dye using Light cycler 96 according to the manufacturer's instructions (Light Cycler® Fast-Start DNA Master SYBR Green I, Roche). The primers used for the analysis are provided in Table 5. The beta actin gene was used as the housekeeping gene. The gene expression of the target gene in each test sample was determined by relative quantification using the comparative Ct ($\Delta\Delta Ct$) method.

RAGE expression was increased in diabetic rats. BAP had no effect on pancreatic RAGE expression AC3 reduced the expression by 30.3%. The combination reduced expression by 44.6 and 76.7% respectively While metformin was effective in reducing by 6.9% (FIG. 1)

TABLE 5

List of Primers for the marker expression

| Si No | Oligo Name | Sequence 5' to 3' |
|---|---|---|
| 1 | R RAGE F | ACAGAAACCGGTGATGAA GG (SEQ ID NO 1) |
|   | R RAGE R | CTCTCCTCGAGTCTGGGTTG (SEQ ID NO 2) |
| 2 | R Beta actin F | CCCGCGAGTACAACCTTCT (SEQ ID NO 3) |
|   | R Beta actin R | CGTCATCCATGGCGAACT (SEQ ID NO 4) |
| 3 | R TNF alpha F | ACTGAACTTCGGGGTGATTG (SEQ ID NO 5) |
|   | R TNF alpha R | GCTTGGTGGTTTGCTACGAC (SEQ ID NO 6) |
| 4 | R IL-6 F | CTCTCCGCAAGAGACTTCCAG (SEQ ID NO 7) |
|   | R IL-6 R | TTCTGACAGTGCATCATCGCT (SEQ ID NO 8) |
| 5 | R IL-1beta F | CACCTTCTTTTCCTTCATCTTTG (SEQ ID NO 9) |
|   | R IL-1beta R | GTCGTTGCTTGTCTCTCCTTGTA (SEQ ID NO 10) |

TABLE 6

Expression levels of Markers

| Marker | Normal | Diabetic | BAP 200 µg/kg | AC3 (100 mg/kg) | AC3 + BAP (100 mg/kg + 50 µg/kg) | AC3 + BAP (100 mg/kg + 200 µg/kg) | Met |
|---|---|---|---|---|---|---|---|
| TNF-α | 1 | 1.73 ± 0.34 | 2.01 ± 0.31 | 1.60 ± 0.36 | 1.33 ± 0.01 | 0.91 ± 0.06 | 0.91 ± 0.22 |
| IL-6 | 1 | 1.60 ± 0.09 | 2.09 ± 0.08 | 1.47 ± 0.14 | 1.25 ± 0.20 | 0.89 ± 0.14 | 1.04 ± 0.12 |
| IL-1β | 1 | 1.66 ± 0.04 | 1.62 ± 0.11 | 1.47 ± 0.18 | 0.73 ± 0.04 | 0.70 ± 0.12 | 0.89 ± 0.05 |

The expression of inflammatory cytokines showed an increase in diabetic rats compared to control. BAP at 200 ug/kg was not effective in reducing the cytokine expression in pancreas, while AC3 was minimally active. The combination was highly effective in reducing the expression levels of inflammatory cytokines (Table 6) (p<0.05).

Example 4: Estimation of Oxidative Stress

The level of oxidative stress in tissue was estimated by using 20,70-dichlorofluorescin diacetate (DCFDA), a fluorogenic dye that measures hydroxyl, peroxyl, and other reactive oxygen species (ROS) activity. Briefly, an aliquot of the tissue homogenates (10 µL) were mixed with 150 µL ethanol solution of DCFDA to the final concentration of 10 mM. After incubation for 30 min at room temperature in dark, the fluorescence was measured with the excitation and emission wavelengths of 488 and 520 nm. Higher the fluorescence, higher is the oxidative stress. oxidative stress is decreased in the subject, and brought about by curcuminoids. BAP, or their combination. The combinations had a better effect with 3-4 fold decrease compared to the BAP with 2 fold decrease from the diabetic control (Table 7).

TABLE 7

Relative Fluorescence Intensity Measuring Oxidative Stress

| Sample | Relative Fluorescence Intensity | |
|---|---|---|
| | Average | Std deviation |
| Normal | 6.5 | 4.2 |
| Diabetic | 23.8 | 3.9 |
| BAP (200 µg/kg) | 11.5 | 1.4 |
| AC3 + BAP (100 mg/kg + 50 µg/kg) | 8.5 | 2.1 |
| AC3 + BAP (100 mg/kg + 200 µg/kg) | 20.8 | 1.8 |
| Met | 28.94 | 1.1 |

Example 5: Protein Carbonylation and AGE-Protein Carbonylation in Pancreas

Protein carbonylation is defined as an introduction of reactive carbonyl moiety, such as an aldehyde, ketone, or lactam, in a protein via oxidative stress-related reactions. Therefore, the term "carbonyl stress" has been suggested to describe the unusual accumulation of reactive carbonyl species due to disturbance of their production or cellular metabolism. Compared to other oxidative modifications, protein carbonyls have unique stability, can circulate in blood for a longer period and a wide range of downstream functional consequences. Chronic diseases like diabetes, lung disease, renal failure, and Alzheimer's disease are some of the consequences of carbonylated proteins. Apart from AGE, hyperglycemia can increase protein carbonylation. In diabetes, increased level of reactive oxygen species (ROS) in combination with hyperglycemia, lead to the formation of reactive carbonyl-containing intermediates such as glyoxal and methylglyoxal (MG) derived from the oxidation of glucose. Thus lowering the Protein carbonyl compounds is being pursued as a novel mechanism for managing chronic diseases.

Fluorimetric NBDH (7-hydrazino-4-nitrobenzo-2,1,3-oxadiazole) Assay of Protein Carbonyls (PCs)

This assay is based on the reaction of NBDH with carbonyls via hydrazone formation to form highly fluorescent products (Vidal et la., 2014). All protein-containing or biological samples were diluted 2-fold in PBS. The 100 µL of diluted protein samples was placed in a black 96-well micro plate. To that 100 µL of NBDH solution (200 µM NBDH in PBS (pH 7.4) with 1 M HCl) was added and incubated at 37° C. for 20 minutes with mild shaking. The fluorescence was measured at 560 nm, exciting at 480 nm. effect of Protein carbonylation was inhibited between 6 to 10-fold when either curcuminoids or BAP are used individually, and the combination provided 20-fold change from the hyperglycemic control (FIG. 2). The combination of AC3 and BAP showed considerable effect than the individual treatment.

Example 6: Activities Against DPP4, α-Glucosidase, and Glycation

The bisdemethoxycurcumin (AC3) composition exhibiting control on hyperglycemia by inhibiting DPP4 enzyme (Table 8), α-glucosidase enzyme (Table 9), and effect of individual curcuminoids, C3 complex, AC3 complex on anti-glycation and DPP4 in a dose dependent manner. AC3 complex was better inhibitor for anti-glycation than individual curcuminoids (Table 10), and curcumin was as effective as AC3 against DPP4 (Table 11)

TABLE 8

Inhibition of DPP4

| AC3 Concentration (µg/ml) | Inhibition (%) |
|---|---|
| 250 | 85.04 |
| 125 | 72.87 |
| 62.5 | 56.43 |
| 31.25 | 39.63 |
| 15.625 | 17.73 |
| IC50 | 43.38 ug/mL |

TABLE 9

Inhibition of Alpha glucosidase activity

| AC3 Concentration (µg/mL) | Inhibition (%) |
|---|---|
| 30 | 34.52 |
| 15 | 11.41 |
| 7.5 | 8.65 |

TABLE 10

Anti-Glycation activity of Curcuminoids at 24 and 72 hrs

| Conc (mg/mL) | Curcumin | BDMC | DMC | C3 Complex | AC3 Complex |
|---|---|---|---|---|---|
| 24 hrs (320/405) | | | | | |
| 0.625 | 35.90 | 77.84 | 84.98 | 74.18 | 98.90 |
| 0.3125 | 29.67 | 62.64 | 73.81 | 61.36 | 92.54 |
| 72 hrs (320/405) | | | | | |
| 0.625 | 44.42 | 42.42 | 57.71 | 47.38 | 92.39 |

TABLE 11

Anti-DPP4 activity of curcuminoids

| Conc (mg/mL) | Curcumin | BDMC | DMC | C3 Complex | AC3 Complex |
|---|---|---|---|---|---|
| 50 | 70.29 | 58.55 | 62.60 | 74.58 | 73.61 |
| 25 | 48.88 | 56.07 | 39.86 | 56.04 | 57.90 |
| 12.5 | 14.11 | 43.58 | 23.56 | 38.27 | 39.99 |

Example 7: Formulations Containing AC3 and β-Amyrin Palmitate

The composition is formulated along with pharmaceutically/nutraceutically acceptable excipients, adjuvants, diluents, stabilizing agents, dispersible gums, bioavailability enhancers or carriers and administered orally in the form of tablets, capsules, syrups, gummies, powders, suspensions, emulsions, chewables, candies or eatables.

In a related aspect the bioavailability enhancer is selected from the group of piperine (BioPerine®), quercetin, garlic extract, ginger extract, and naringin. In another related aspect, the stabilizing agent is selected from the group consisting rosmarinic acid, butylated hydroxyanisole, butylated hydroxytoluene, sodium metabisulfite, propyl gallate, cysteine, ascorbic acid and tocopherols. In yet another related aspect, the dispersible gums are selected from the group consisting of Agar, Alginate, Carrageenan. Gum Arabic, Guar Gum. Locust Bean Gum, Konjac Gum, Xanthan Gum and Pectin.

Tables 12-16 provide illustrative examples of nutraceutical formulations containing bisdemethoxycurcumin

TABLE 12

Tablet

Active Ingredients

AC3, β-Amyrin Palmitate
Excipients

Microcrystalline cellulose, Colloidal silicon dioxide, Magnesium stearate, BioPerine®, Polyvinylpyrrolidone/starch/Hydroxy propyl methyl cellulose, Hydroxy propyl cellulose

TABLE 13

Capsule

Active Ingredients

AC3, β-Amyrin Palmitate
Excipients

Microcrystalline cellulose, BioPerine®

TABLE 14

Powder

Active Ingredients

AC3, β-Amyrin Palmitate
Excipients

BioPerine®,

TABLE 15

Gummy formulation

Active Ingredients

AC3, β-Amyrin Palmitate
Excipients

BioPerine®, Gelatin (270 Bloom Mesh 10), Refined Sugar, Glucose Corn Syrup, Citric Acid, Lactic Acid, Water, Natural Mango Flavor M38630, Tartaric Acid, Refined Sugar

TABLE 16

Candy formulation

Active Ingredients

AC3, β-Amyrin Palmitate
Excipients

BioPerine®, Sucrose, Liquid Glucose, Flavoring agent, Menthol, Acidulants (Citric acid/Tartaric Acid/Maleic Acid), Purified water The above formulations are merely illustrative examples, any formulation containing the above active ingredient intended for the said purpose will be considered equivalent.

Other modifications and variations of the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention and is to be interpreted only in conjunction with the appended claims.

SEQUENCE LISTING

SEQ ID NO 1: FORWARD PRIMER FOR RAGE
acagaaaccg gtgatgaagg
SEQ ID NO 2: REVERSE PRIMER FOR RAGE
ctctcctcga gtctgggttg
SEQ ID NO 3: FORWARD PRIMER FOR BETA ACTIN
cccgcgagta caaccttct
SEQ ID NO. 4: REVERSE PRIMER FOR BETA ACTIN
cgtcatccat ggcgaact SEQ ID NO. 5: FORWARD PRIMER FOR TNF ALPHA
actgaacttc ggggtgattg
SEQ ID NO. 6: REVERSE PRIMER FOR TNF ALPHA
gcttggtggt ttgctacgac
SEQ ID NO. 7: FORWARD PRIMER FOR IL6
ctctccgcaa gagacttcca g
SEQ ID NO. 8: REVERSE PRIMER FOR IL6
ttctgacagt gcatcatcgc t SEQ ID NO. 9: FORWARD PRIMER FOR IL1 BETA
caccttcttt tccttcatct ttg
SEQ ID NO. 10: REVERSE PRIMER FOR IL1 BETA
gtcgttgctt gtctctcctt gta The sequence listing in the CRF is incorporated herein by reference. The details of the CRF is below:
i) Name of the ASCII text file: SEQ_LISTING
ii) Date of Creation: 15 Dec. 2021
iii) Size: 2,302 bytes

We claim:

1. A method for inhibiting Receptor for Advanced Glycation End products (RAGE) expression in a subject with chronic inflammatory condition, comprising: (a) identifying said subject with the chronic inflammatory condition; b) administering to said subject with a composition comprising enriched Bisdemethoxycurcumin (BDMC) present not less than 20% w/w and β-amyrin palmitate (BAP).

2. The method as claimed in claim 1, wherein the composition comprises of 20-50% w/w BDMC, 10-25% w/w demethoxycurcumin (DMC) and 30-50% w/w curcumin, with the total curcuminoids in the composition are in the range of 20-95% w/w.

3. The method as claimed in claim 1, wherein inhibition of RAGE expression results in decreasing expression of inflammatory markers, decreasing oxidative stress, and moderating glycation levels.

4. The method as claimed in claim 1, wherein inhibition of RAGE expression is brought about by curcuminoids and BAP, each selected from the range of 1-10 μg/mL.

5. The method as claimed in claim 1, wherein inhibition of RAGE expression is brought about by treating with curcuminoids and BAP each selected from the range of 50 μg/kg-100 mg/kg.

6. The method as claimed in claim 3, wherein the inflammatory marker is selected from the group consisting of TNF-α, IL-6, and IL-1β, wherein the decrease of the inflammatory marker expression is brought about by treating with curcuminoids and BAP, each selected from the group consisting of 50 μg/kg-100 mg/kg.

7. The method as claimed in claim 3, wherein the oxidative stress is decreased in the subject by treating with curcuminoids and BAP, each selected from the range of 50 μg/kg-100 mg/kg.

8. The method as claimed in claim 3, wherein moderating glycan levels is brought about by treating with curcuminoids and BAP, each selected from the range of 50 μg/kg-100 mg/kg.

9. The method as claimed in claim 1, wherein chronic inflammatory condition is selected from the group consisting of type II diabetes mellitus, cardiovascular diseases Alzheimer's disease, cancer, peripheral neuropathy, sensory losses and blindness.

10. The method as claimed in claim 1, wherein the subject is a mammal.

11. The method as claimed in claim 1, wherein the composition further comprises of stabilizing agents, bioavailability enhancers and antioxidants, pharmaceutically or nutraceutically or cosmeceutically accepted excipients and enhancers and administered orally in the form of tablets, capsules, syrups, gummies, powders, suspensions, emulsions, chewables, candies or eatables.

12. A method of treating chronic inflammatory condition in a subject, comprising: (a) identifying said subject, b) administering said subject with a composition comprising enriched Bisdemethoxycurcumin (BDMC) present not less than 20% w/w and β-amyrin palmitate (BAP).

13. The method as claimed in claim 12, wherein the composition comprises of 20-50% w/w BDMC, 10-25% w/w demethoxycurcumin (DMC) and 30-50% w/w curcumin, with the total curcuminoids in the composition are in the range of 20-95% w/w.

14. The method as claimed in claim 12, wherein treating chronic inflammatory condition in the subject is brought about by inhibiting RAGE expression, decreasing expression of inflammatory markers, decreasing oxidative stress, and moderating glycation levels.

15. The method as claimed in claim 14, wherein the inhibition of RAGE is brought about by curcuminoids and BAP, each selected from the range of 1-10 μg/mL.

16. The method as claimed in claim 14, wherein moderating RAGE expression is brought about by treating with curcuminoids and BAP, each selected from the range of 50 μg/kg-100 mg/kg.

17. The method as claimed in claim 14, wherein the inflammatory marker is selected from the group consisting of TNF-α, IL-6, and IL-1β, wherein the decrease of the inflammatory marker expression is brought about by treating with curcuminoids and BAP, each selected from the range of 50 μg/kg to 100 mg/kg.

18. The method as claimed in claim 14, wherein the oxidative stress is decreased in the subject by treating with curcuminoids and BAP, each selected from the range of 50 μg/kg-100 mg/kg.

19. The method as claimed in claim 14, wherein moderating glycan levels is brought about by treating with curcuminoids and BAP, each selected from the range of 50 μg/kg-100 mg/kg.

20. The method as claimed in claim 12, wherein chronic inflammatory condition is selected from the group consisting of type II diabetes mellitus, cardiovascular diseases Alzheimer's disease, cancer, peripheral neuropathy, sensory losses and blindness.

21. The method as claimed in claim 12, wherein the subject is a mammal.

22. The method as claimed in claim 12, wherein the composition further comprises of stabilizing agents, bioavailability enhancers and antioxidants, pharmaceutically or nutraceutically or cosmeceutically accepted excipients and enhancers and administered orally in the form of tablets, capsules, syrups, gummies, powders, suspensions, emulsions, chewables, candies or eatables.

* * * * *